(12) United States Patent
Donelon et al.

(10) Patent No.: US 6,658,916 B2
(45) Date of Patent: Dec. 9, 2003

(54) OXYGEN SENSOR FOR MULTIPLE PORT APPLICATIONS

(75) Inventors: Matthew J. Donelon, Wichita Falls, TX (US); Kathryn McCauley, Durand, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/737,520

(22) Filed: Dec. 15, 2000

(65) Prior Publication Data

US 2002/0073763 A1 Jun. 20, 2002

(51) Int. Cl.[7] .................. G01N 30/02; G01N 27/04; G01M 19/00; G01M 15/00
(52) U.S. Cl. ................ 73/23.31; 73/31.05; 73/23.31; 422/94; 204/424
(58) Field of Search .................. 73/23.31, 23.32, 73/31.05, 23.2; 204/424, 426, 429; 422/94

(56) References Cited

U.S. PATENT DOCUMENTS

| | | | |
|---|---|---|---|
| 4,214,472 A | * 7/1980 | Maxwell et al. | 73/23 |
| 4,236,138 A | * 11/1980 | Segawa et al. | 338/34 |
| 4,237,722 A | * 12/1980 | Achari | 73/23 |
| 4,308,518 A | * 12/1981 | Hattori et al. | 338/34 |
| 4,443,781 A | * 4/1984 | Ohta et al. | 338/34 |
| 4,532,492 A | * 7/1985 | Esper et al. | 338/34 |
| 4,591,423 A | 5/1986 | Kato et al. | 204/428 |
| 4,597,850 A | 7/1986 | Takahasi et al. | 204/426 |
| 4,697,165 A | * 9/1987 | Ishiguro et al. | 338/34 |
| 4,883,643 A | * 11/1989 | Nishio et al. | 422/94 |
| 5,467,636 A | * 11/1995 | Thompson et al. | 73/23.31 |
| 5,490,412 A | * 2/1996 | Duce et al. | 73/23.31 |
| 5,518,603 A | 5/1996 | Furuhashi et al. | 204/429 |
| 5,602,325 A | * 2/1997 | McClanahan et al. | 73/23.31 |
| 5,616,825 A | * 4/1997 | Achey et al. | 73/23.31 |
| 5,739,414 A | * 4/1998 | Paulus et al. | 73/23.31 |
| 5,817,920 A | * 10/1998 | Kuisell et al. | 73/23.31 |
| 5,821,401 A | 10/1998 | Awarzamani et al. | 73/23.32 |
| 5,874,663 A | * 2/1999 | Fukaya et al. | 73/23.32 |
| 5,886,248 A | * 3/1999 | Paulus et al. | 73/23.31 |
| 5,948,963 A | * 9/1999 | Kato et al. | 73/23.2 |
| 5,949,023 A | 9/1999 | Weyl | 174/77 R |
| 5,955,656 A | * 9/1999 | Graser et al. | 73/23.31 |
| 6,032,514 A | * 3/2000 | Weyl et al. | 73/31.05 |
| 6,063,249 A | 5/2000 | Duce et al. | 204/424 |
| 6,065,327 A | * 5/2000 | Fukaya et al. | 73/23.32 |
| 6,153,071 A | 11/2000 | Omara et al. | 204/424 |
| 6,153,861 A | * 11/2000 | Weyl | 219/505 |
| 6,178,806 B1 | * 1/2001 | Watanabe et al. | 73/23.32 |

FOREIGN PATENT DOCUMENTS

| | | |
|---|---|---|
| DE | 19523979 | 1/1997 |
| DE | 29521966 | 2/1999 |
| EP | 0704698 | 4/1996 |

* cited by examiner

Primary Examiner—Hezron Williams
Assistant Examiner—David J. Wiggins
(74) Attorney, Agent, or Firm—Vincent A. Cichosz

(57) ABSTRACT

A sensor comprising; a sensing element disposed within a housing having a lower shell portion, a middle shell portion, and an upper shell portion, wherein said sensing element extends from said lower shell portion through at least a portion of said middle shell portion; a connector plug concentrically disposed within said upper shell portion; one or more electrical wires extending from said connector plug through an opening in said upper shell portion, and said opening forming a seal in said upper portion concentrically disposed around said one or more eletrical wires.

13 Claims, 2 Drawing Sheets

OXYGEN SENSOR FOR MULTIPLE PORT APPLICATIONS

TECHNICAL FIELD

The present disclosure relates generally to exhaust gas sensors capable of detecting and measuring exhaust gas compositions, and more particularly, relates to an improved compact design for exhaust gas sensors.

BACKGROUND

Automotive vehicles with an internal combustion engine have an exhaust system that includes a pathway for exhaust gas to move away from the engine. The temperature of the exhaust gases ranges from ambient temperature, when the engine has not been run recently, to higher than 1000° C. Frequently used in these exhaust systems is an Exhaust Gas Oxygen (EGO) sensor assembly, which allows for a determination of a rich or lean air/fuel ratio.

The sensing element of an EGO sensor consists of a dense oxygen-conducting zirconia (ZrO2) ceramic, most commonly cylindrically shaped having an opening at one end and having a rounded closure at the other end, with porous platinum electrodes, one on the outside and the other on the inside surfaces of the cylinder. The outside electrode is covered with a porous layer of spinel or magnesia alumina oxide, typically applied either by thermal spray deposit or a co-fired slurry dip coating. The materials are commercially available from many sources. This sensing element is mounted within a housing structure that seals the inside of the cylinder from the outside of the cylinder. When the EGO sensor is mounted onto the exhaust manifold of an engine, the outer electrode is exposed to the exhaust stream whereas the inner electrode is exposed to the ambient air as a reference oxygen atmosphere. When the air/fuel ratio is lean, the EGO sensor voltage output has a small value (e.g. 50 mV) because the oxygen partial pressure in the exhaust gas is not significantly different from the oxygen pressure in the air. When the air/fuel is rich, the EGO voltage output is large (e.g., 700–900 mV) because the thermodynamic equilibrium oxygen partial pressure of the exhaust gas is many orders of magnitude smaller than that of the air reference. Consequently, when the air/fuel ratio varies from the optimal stoichiometric ratio (e.g., 14.7:1), the EGO sensor output changes abruptly between a large and a small value. This sensor output signal is conveyed by means of an associated set of electrical output leads. This signal is then used by the engine control system to adjust the air/fuel ratio being supplied to the combustion chambers of the engine to a desired air/fuel ratio, generally very close to the stoichiometric air/fuel ratio.

Most current EGO sensors also include a heater that is inserted in the air reference. The heater assists the zirconia sensor, a heated exhaust gas oxygen (HEGO) sensor, in making more precise measurements over a wide range of exhaust gas temperatures, especially when the exhaust gas temperature is low. The addition of the heater also helps to decrease the light-off time of the sensor, that is the time that it takes for the sensor to reach the minimum temperature for proper operation.

EGO sensors are typically in direct contact with extremely hot exhaust gases and exhaust gas piping, and in some designs, with supplemental heat generated by a heater rod positioned within the lower region of the sensor itself. Consequently, these sensors are designed to protect heat sensitive components of the sensor from the extreme conditions of the operating environment. Typically, the sensor components having the lowest heat resistance are located in the upper region of the sensor. Such components include the grommet or cable seal, which generally comprises an elastomeric material such as Viton® rubber, and the cable insulation, which often comprises Teflon® (i.e., a fluorocarbon polymer) or similar material. The design parameters, e.g., the size and geometry, of typical EGO sensors are similarly limited by the various temperature constraints. For example, the sensor often has a sufficient height to remove the heat sensitive components in the upper region from the hot exhaust gas.

FIG. 1 shows a conventional heated exhaust sensor 10 having three wires extending therefrom, wherein two of the wires are for heating a sensing element 36 and the third wire is an engine management system (EMS) input generating its own low voltage signal. It will be understood that a single wire exhaust sensor is grounded to the exhaust manifold. Exhaust sensor 10 comprises a three-piece housing structure comprising an upper tubular shell 19, a middle shell 26 and a lower tubular shell 31. The metal housing has a longitudinal bore 36 with a sensing element 30 disposed therein. An electrically insulating ceramic material 24 is concentrically disposed around longitudinal bore 36 to support the sensing element 30. Sensing element 30 is an exhaust sensing element of a known type with any conventional geometry, such as a generally flat elongated rectangular shape.

Lower tubular shell 31 has disposed therein a first section 30a of sensing element 30. At section 30a thereof, sensing element 30 includes an exhaust constituent-responsive structure fabricated into sensing element 30 in a known manner, preferably along with a heater rod 29 of a known type. The lower tubular shell 31 includes perforations 33 formed therein through which exhaust gas enters and contacts the sensing element 30. Exhaust gas temperatures contacting lower tubular shell 31 may reach levels of about 1000° C. The middle shell 26 includes wrench flats 34 and a threaded portion 35 for threading into a manifold boss of an exhaust system (e.g., pipe of manifold). Upper tubular shell 19 extends from middle shell 26 to cable seal 13. Upper tubular shell 19 houses a second section 30b of sensing element 30, connector plug 32, electrical wires 12, and cable seal 13. Upper tubular shell 19 is concentrically disposed around cable seal 13, typically an elastomeric component, and is in direct contact therewith, securing it in place. Electrical wires 12 pass through cable seal 13 into connector plug 32 to form an electrical connection with sensing element 30 through electrical terminals 16.

An outer shield 14 is concentrically disposed around upper tubular shell 19 to protect exhaust gas sensor 10 from the high temperature exhaust gas environment. Typically, outer shield 14 is concentrically disposed around upper tubular shell 19 from about the upper one-half to about the upper one-third of upper tubular shell 19. An insulating material 15, such as a breathable Teflon® (i.e., a fluorocarbon polymer) material, is disposed between outer shield 14 and upper tubular shell 19 at nearly all points. Outer shield 14 and upper tubular shell 19 are in direct physical contact at the lower end 37 of outer shield 14.

In the typical manner of use, lower tubular shell 31 of the exhaust gas sensor 10, is contacted with very hot exhaust gases generated by an engine. Contact with exhaust gases allows sensing element 30 to measure the component gases. During this process, substantial heat is undesirably conducted from lower tubular shell 31 to middle shell 26, and further to upper tubular shell 19. As upper tubular shell 19 is in direct contact with cable seal 16, substantial heat is also conducted from upper tubular shell 19 to cable seal 16 and to electrical wires 12 disposed therein. Such conduction of extreme heat from lower tubular shell 31 to cable seal 16 and electrical wires 12 is highly undesirable due to the low heat resistance of cable seal 16 and wires 12 relative to other components of exhaust gas sensor 10. As cable seal 16 and wires 12 are typically the first components of exhaust gas sensor 10 to deteriorate under high temperature operation, the reduction of heat conduction to them is advantageous. The reduction of heat conduction to the wires is typically gained by increasing the distance the wires are from the lower tubular shell 31 by increasing the length of an EGO sensor. An EGO sensor with a reduced size, however, would be advantageous for use in each exhaust cylinder port for monitoring the air/fuel ratio in each cylinder.

Because of the cost and size of a typical EGO sensor, one sensor is usually installed after an exhaust manifold converges to one pipe ("engine out" ) in a vehicle exhaust system to monitor the air/fuel ratio of the engine as a whole, rather than in any one of the runners which would sense exhaust gas in any cylinder individually. Another sensor may be installed after the catalytic converter ("post converter" ). The cost and dimensions of current EGO sensors do not facilitate the installation of an EGO sensor in each cylinder port of an exhaust manifold where monitoring the air/fuel ratio of each cylinder individually is advantageous.

What is needed in the art is an improved EGO sensor design that is small enough, cost effective, durable and serviceable for use in each exhaust manifold port for each cylinder of an engine.

SUMMARY

EGO sensors are desirably employed in connection with each cylinder of an engine enabling an engine management system (EMS) to optimize the air/fuel ratio in each cylinder and thereby improve performance and fuel economy of each of the cylinders individually and therefore the engine as a whole. An EGO sensor for a multiport application comprises: a sensing element disposed within a housing having a lower shell portion, a middle shell portion, and an upper shell portion, wherein said sensing element extends from said lower shell portion through at least a portion of said middle shell portion; a connector plug disposed within said upper shell portion; one or more electrical wires extending from said connector plug and through an opening in said upper shell portion disposed on a side of said connector plug opposite said middle shell portion, and said opening forming a seal in said upper portion disposed around said one or more electrical wires.

BRIEF DESCRIPTION OF THE DRAWINGS

Referring to the accompanying drawings, which are meant to be exemplary, not limiting, wherein like elements are numbered alike in the several Figures.

DESCRIPTION OF THE PREFERRED EMBODIMENT

An improved EGO (or other exhaust gas) sensor 40 for use in a closed loop control on each cylinder of a multiple cylinder engine is disclosed herein. When the engine is first started and the rpm is above a predetermined value stored in the EMS's memory, the system operates in an "open loop mode. In "open loop mode, the EMS ignores the exhaust sensor, and calculates the air/fuel ratio based on inputs from other engine sensors. When the "closed loop" conditions and values are met as determined by the EMS on the basis of inputs from other engine sensors such as temperature sensors, the system begins to operate in a "closed loop mode. In this mode, the EMS calculates the fuel/air ratio based on the signal from the EGO sensor.

Figure 2:
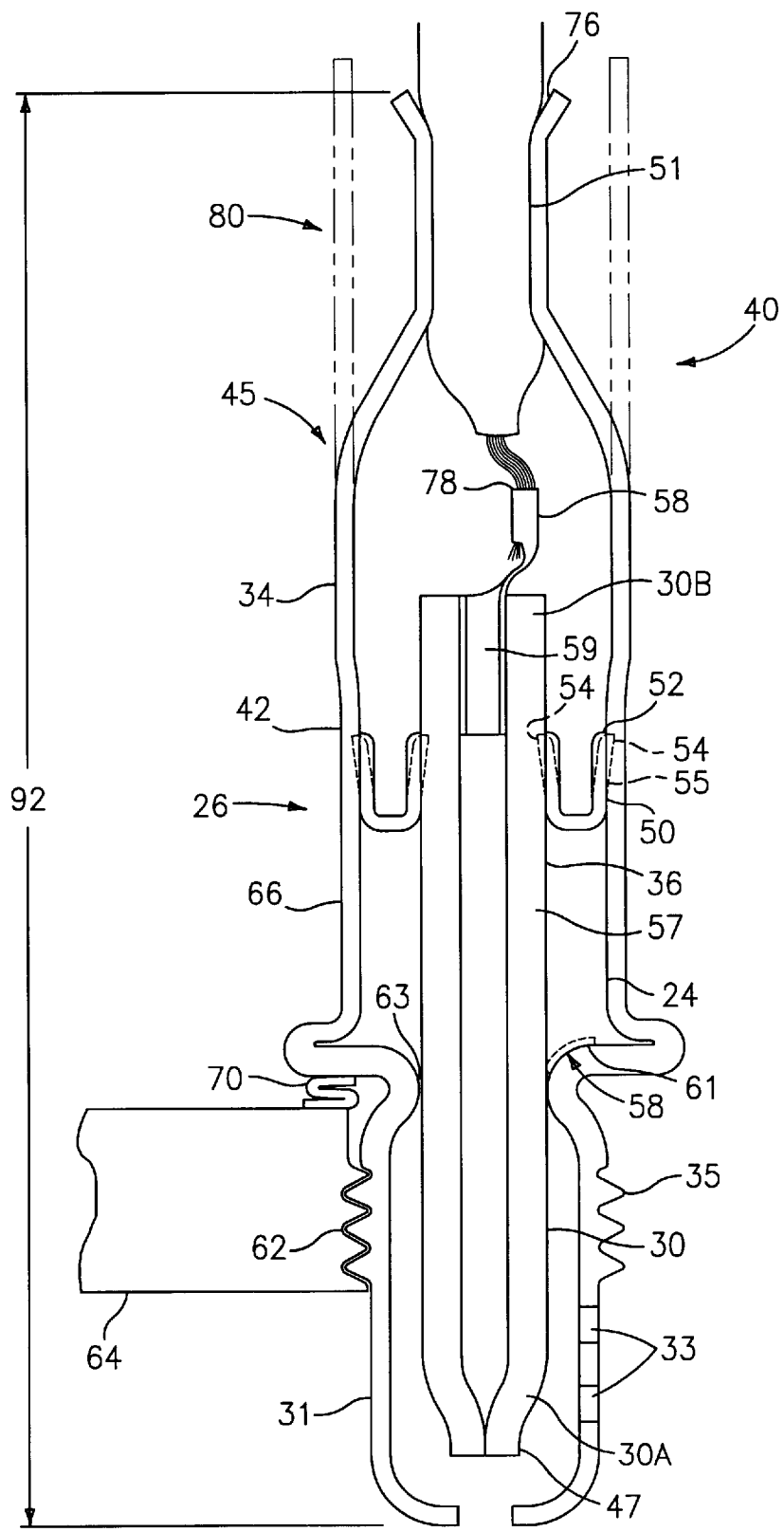
FIG. 2 is a cross-sectional view of one embodiment of an exhaust gas sensor for multiple port applications.

Referring to FIG. 2, the improved EGO sensor 40 includes a single piece housing 42, which for illustrative and relative positioning purposes is referred to as comprising an upper tubular shell portion 45, a middle shell portion 26 and a lower tubular shell portion 31. Preferred materials for housing 42 include inconel sheet metal, ferrous materials, chrome, nickel, and other metals, and mixtures and alloys comprising at least one of the foregoing, with high chrome or nickel stainless steel preferred; wherein the steels are chosen for high temperature resistance, corrosion resistance, and impact resistance. Furthermore, the housing 42 optionally has a variable wall thickness . The housing 42 has a longitudinal bore 36 with a sensing element 30 disposed therein. Sensing element 30 is an exhaust sensing element configured in a tubular shape preferably formed utilizing current extrusion techniques. Ceramic extrusion enables tubular-shaped element fabrication with an inexpensive technique. The ceramic extrusion technique is a commonly used generic industry standard. Alternative methods, such as mold-and grind (currently used) or compaction pressed (inexpensive, but limited accommodation for preferred embodiment geometry) may be utilized. A tubular-shaped element also allows an inexpensive compact package design, although it should be understood that other post-process enhancements can be made. An end 47 of the extruded tube sensing element 30 is either pinched closed or zirconia slurry dipped to close the end sufficiently to prevent particulate matter from entering the inside of the extruded tube. Furthermore, in addition to the aforementioned conventional component processing, additional conventional component processing is preferably employed, including, but not limited to having the sensing element 30 bisque fired, ink dip coated, fired, sputtered, plasma sprayed, alumina coated, N2 aged, and the like, as well as combinations comprising one of the foregoing.

Still referring to FIG. 2, an electrically insulating material 24 is disposed within middle shell portion 26 in longitudinal bore 36 to support the sensing element 30. This insulating material can be any material capable of sealing, providing thermal insulation and providing the desired structural integrity. Possible materials include talc, polymers, ceramics and the like, as well as other conventional materials. In a preferred embodiment, insulating material 24 is a talc pack, compressed to make a seal. A press ring 50 is used to secure the talc pack with minimal springback loss. Press ring has barbs 54 circumferentially disposed on an outside edge 55 of press ring 50 to frictionally engage an interior surface 52 of middle shell portion 26. Press ring 50 optionally further comprises barbs 54 circumferentially disposed within an opening configured to engage sensing element 30?. The barbs 54 are configured and oriented to prevent press ring 50 from translating away from lower tubular shell portion 31 once installed in the orientation depicted. Press ring 50 also functions as the case ground when, for example, electrically conducting ink is disposed on an exterior surface 57 of sensing element 30 where press ring 50 engages sensing element 30. In the event the sensing element 30 is to be grounded through press ring 50, sensing element 30 must be coated with the electrically conductive ink such that the ink is disposed on the exterior surface 57 where press ring 50 engages surface 57 to provide an electrical communication to the housing 42. Alternatively, a grounding gasket 58 may be employed as a case ground. Grounding gasket 58 is preferable in some applications due to a location relative to sensing element 30, which requires that less of sensing element 30 be coated with conductive ink. The conductive ink itself is an expensive component of the EGO sensor. Grounding gasket 58 is disposed on a shoulder 61 formed in middle shell portion 26 of housing 42. Shoulder 61 is formed on the interior surface 52 where bore 36 narrows providing a barrier 63 between lower shell portion 31 that is exposed to hot exhaust gases and middle shell portion 26, which preferably is shielded from exhaust gases. It should be noted that there are no ceramic components other than the sensing element 30 in a preferred embodiment.

Lower tubular shell portion 31 can include perforations 33 (e.g., louvers, slits, holes, etc.) formed therein through which exhaust gas enters and contacts the sensing element 30.

Upper tubular shell 45 houses a second section 30b of sensing element 30, connector plug 58, and one or more electrical wires 51. As shown in FIG. 2, electrical wire 51 passes through an opening 76 formed in the upper tubular shell portion 45 into connector plug 58 to form an electrical connection with sensing element 30 through electrical terminal 59. Electrical terminal 59 is a gripper-style signal terminal. In the particular embodiment illustrated in FIG. 2, upper tubular shell portion 45 extends beyond a top portion 78 of connector plug 58. It should be noted that while the upper tubular shell 45 is depicted to extend beyond connector plug 58, the exact point to which it extends may vary according to design preference and desired thermal control. Forming opening 76 is a crimped section 80 of upper tubular shell portion 45 (as shown by phantom lines) to form a water resistant seal concentrically disposed around wire 51. A water resistant seal is preferable to a waterproof seal in the illustrated embodiment for cost reasons in conjunction with the planned location of the sensor in the automobile.

Figure 1:
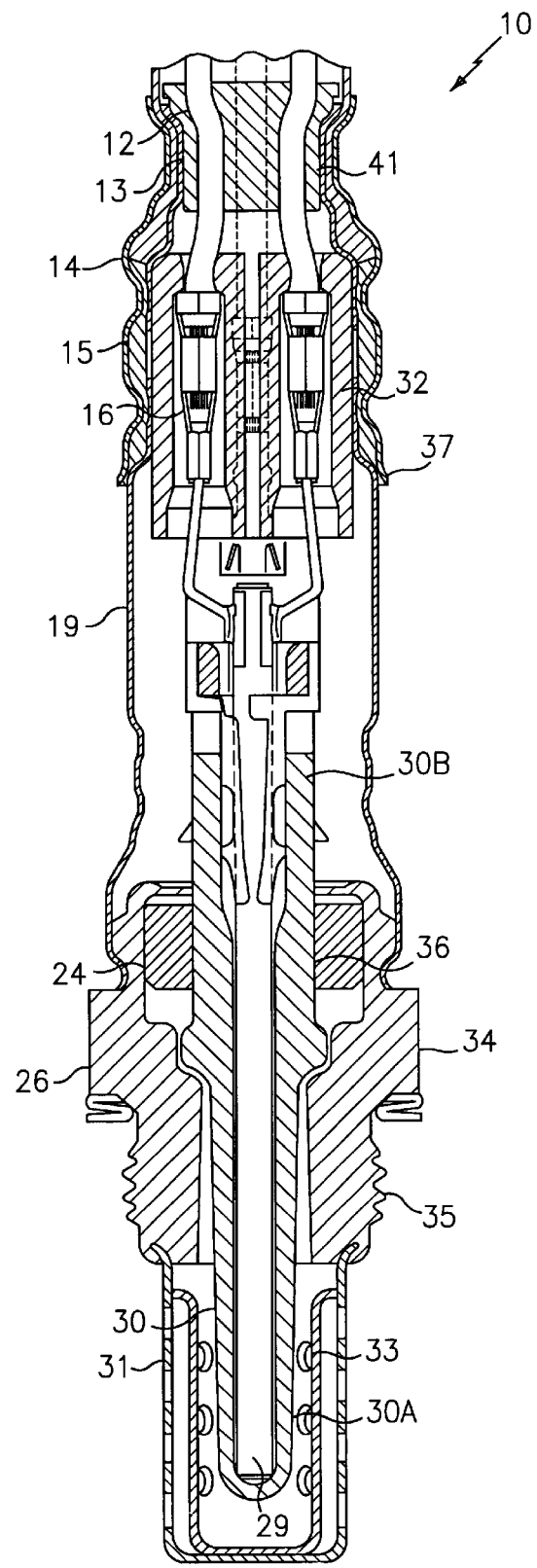
FIG. 1 is a cross-section view of a conventional heated exhaust gas sensor having two heater wire and a sensor wire.

In the manner of use, lower tubular shell 31 of the EGO sensor 40, is contacted with very hot exhaust gases generated by an engine. Contact with exhaust gases allows sensing element 30 to measure the component gases. During sensing, substantial heat conducts from lower tubular shell portion 31 to middle shell portion 26 to upper tubular shell portion 45. Heat conducted along this pathway is also conducted to electrical wire 51, which is in contact with upper tubular shell portion 45. Thus, in order to assure longevity in the sensor, a wire couple similar to thermocouple wire is utilized. Thermocouple wire typically has a metal conductor core surrounded by an insulating powder (i.e., magnesium oxide), which is surrounded by a protective metal layer. Thermocouple wire can be purchased in various configurations, with materials chosen for temperature and moisture resistance in a preferred embodiment. Advantageously, there is no need for a rubber seal and/or Teflon® (i.e., a fluorocarbon polymer) or similar material, as found in the prior art. Because of the elimination of a cable seal and insulation protecting the wire and seal, (i.e., cable seal 41 and insulation 15 in FIG. 1), the sensor may be assembled in a more compact manner. Although the sensor has been described as having a general tubular geometry, i.e., the tubular shell portions, it is understood that the geometry can vary according to the design parameters.

The middle shell portion 26 of housing 42 further includes a threaded portion 35 to engage with complementary threads 62 in each cylinder port of an exhaust manifold 64. Middle shell portion 26 optionally includes wrench flats 34 and/or a knurled surface 66 formed therein for aid in turning the exhaust sensor to engage or disengage threads 62 of the exhaust manifold 64.

The improved exhaust gas sensor design is advantageous in that it has a lower cost than a typical EGO sensor, both because of its simplicity and use of less material. Furthermore, due to the smaller size of the EGO disclosed herein, both in diameter and length it is capable of fitting on each runner of an exhaust manifold proximate each cylinder port. In an exemplary embodiment, the length 92 of an improved EGO sensor measures 30 mm. Because of the smaller size of the EGO sensor disclosed herein it is mountable in each runner of an exhaust manifold as noted above. Since such a sensor has not heretofore been known, and an exhaust manifold does not currently exist which provides for the desired location of mounting of the sensor. Thus, in order to accommodate the sensor a hole is cast in each runner of a manifold (not shown) proximate a mounting surface of said manifold to each combustion chamber exhaust outlet of an engine. Each hole is preferably tapped to facilitate threaded engagement and retention of an EGO sensor in each runner of the exhaust manifold extending from a cylinder exhaust port to monitor and optimize the air/fuel ratio control in each cylinder of a multiple cylinder engine. While such tapping of the manifold runner hole may be desirable it may be necessary in some manifolds to locally increase wall thickness slightly to provide sufficient thread to retain the sensor. In an alternative embodiment, a boss (not shown) is employed in each hole of an exhaust manifold for attaching an EGO sensor. In either case, a mounting gasket 70 is preferably employed when attaching an EGO sensor into each exhaust manifold hole to prevent hot exhaust gases from escaping from the manifold.

By monitoring the air/fuel ratio in each cylinder exhaust port, an EMS optimizes the air/fuel ratio in each cylinder and thereby improves performance and fuel economy. Specifically, the air/fuel ratio in each cylinder is maintained as other components such as fuel injectors wear. EMS diagnostics are enabled from the information gained at each cylinder individually as opposed to collectively to identify, for example, fuel injectors that leak more than an established rate by comparing to the other cylinders and other engine sensors and therefore to compensate for wear and still optimize engine performance. Furthermore, utilizing an EMS in conjunction with an EGO in each cylinder port allows for relaxed tolerances, and thus lower cost, in manufacturing fuel injectors because of the compensation capability noted above. Similarly, a reduction in exhaust converter size and/or metals loading is obtainable by optimizing the air/fuel ratio in each cylinder facilitated by monitoring the same.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is claimed is:

1. A sensor, comprising:
   a sensing element disposed within a single piece housing having a lower shell portion, a middle shell portion, and an upper shell portion, wherein said sensing element extends from said lower shell portion through at least a portion of said middle shell portion;

a connector plug disposed within said upper shell portion in electrical connection with said sensing element;

one or more electrical wires extending from said connector plug and through an opening in said upper shell portion; and a seal formed between said opening and said one or more wires by interior engagement between said single piece housing defining said opening and a periphery of said one or more wires.

2. A sensor according to claim 1, wherein said seal is formed when upper shell portion is crimped to form said opening and engage said one or more wires.

3. A sensor according to claim 1, wherein said housing comprises inconel sheet metal.

4. A sensor according to claim 1, wherein said housing comprises a ferrous material selected from high chrome steel, nickel stainless or mixture thereof.

5. A sensor according to claim 1, wherein said on e or more electrical wires includes thermocouple wires.

6. A sensor according to claim 1, further comprising insulating material disposed between said sensing element and said middle shell portion.

7. A sensor according to claim 1, wherein said opening formed in said upper shell portion of said single piece housing is adaptable to form said seal.

8. A sensor according to claim 6, wherein said insulating material is a talc pack.

9. A sensor according to claim 6, wherein said insulating material is selected from the group consisting of polymers, ceramics, or a mixture comprising at least one of the foregoing.

10. A sensor according to claim 8, wherein said insulating material is compressed towards said lower shell portion and is retained by a press ring engaged between the sensing element and the middle shell portion.

11. A sensor according to claim 10, wherein said press ring frictionally engages the sensing element and the middle shell portion; said press ring further comprising barbs to prevent movement thereof.

12. A sensor according to claim 10, wherein said insulating material is compressed towards said lower shell portion against a grounding gasket that electrically engages the sensing element and a shoulder formed in said middle shell portion of said housing.

13. A sensor according to claim 1, wherein said seal is formed by crimping said upper shell portion of said single piece housing forming said seal between said opening and insulation of said one or more wires defining a periphery of said one or more wires.

* * * * *